United States Patent [19]

Rotman

[11] Patent Number: 4,609,740

[45] Date of Patent: Sep. 2, 1986

[54] DERIVATIVES OF FLUORESCEIN

[75] Inventor: Avner Rotman, Rehovot, Israel

[73] Assignee: Yeda Research and Development Company Ltd., Rehovot, Israel

[21] Appl. No.: 380,472

[22] Filed: May 20, 1982

[51] Int. Cl.$^4$ .......................................... C07D 311/82
[52] U.S. Cl. ................................................... 549/223
[58] Field of Search ........................................ 549/223

[56] References Cited

PUBLICATIONS

Jour. Chem. Soc. (C) (1970), pp. 654–656.
Carl R. Noller, "Chemistry of Organic Compounds", (1965), pp. 542 and 690.
A. Rotman et al., FEBS Letters, vol. 122, (2) Dec. 1980, pp. 215–217.
A. Rotman et al., Chemical Abstracts, vol. 94 (1981), 152853j.
A. Rotman et al., Biochemistry (1981), vol. 20, pp. 5995–5999.
A. Rotman et al., Biochimica et Biophysica Acta(C), vol. 720, No. 1, Feb. 10, 1982, pp. 75–80.

*Primary Examiner*—Norma S. Milestone
*Attorney, Agent, or Firm*—Browdy and Neimark

[57] ABSTRACT

The invention relates to derivatives of fluorescein and to their production. The compounds are of value in determining the intracellular pH. Thus there may be obtained fluorescent living cells with a comparatively stable level of fluorescence. The novel fluorescein compounds can be used for other labelling purposes in biology and biochemistry.

2 Claims, No Drawings

DERIVATIVES OF FLUORESCEIN

FIELD OF THE INVENTION

The present invention relates to novel derivatives of fluorescein and to the preparation of these. The novel compounds are of value in determining the intracellular pH, as some of the novel derivatives easily penetrate the cell. Thus there may be obtained fluorescent living cells with a comparatively stable level of fluorescence. The novel fluorescein compounds can be used for other labelling purposes in biology and biochemistry. The invention further relates to a process for the production of the novel compounds starting with fluorescein amine. Other and further aspects of the invention will become apparent hereinafter.

SUMMARY OF THE INVENTION

The invention relates to the production of certain novel derivatives of fluorescein, starting with fluorescein amine. Amongst the novel compounds there are: azidofluorescein, its diacetate, and azidofluorescein nitrene which latter is obtained by suitable irradiation. The invention relates to the following as novel compounds:

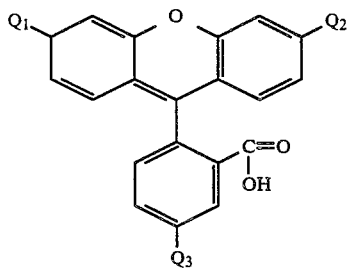

wherein $Q_1$ and $Q_2$ are either:

a. both are —OAc; and $Q_3$ is —$N_3$;

b. one is —OH, the other =O and $Q_3$ is —$N_3$ or nitrene.

DESCRIPTION OF THE PREFERRED EMBODIMENT

The following examples illustrate the preparation of the compounds of the present invention:

Synthesis of Azidofluorescein Diacetate

Fluorescein amine (I) is diazotized with amyl nitrite in low pH to form diazo fluorescein (II) which is converted with sodium azide to azido fluorescein (III). Azidofluorescein is acetylated with acetic anhydride ($Ac_2O$) and Pyridine (Py) to form azidofluorescein diacetate (IV).

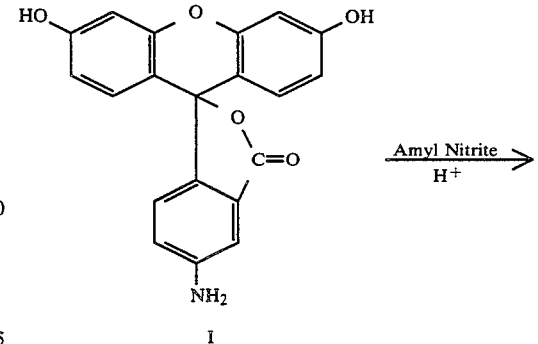

Azidofluorescein

Fluorescein amine (isomer I, 100 mg) was dissolved in 5 ml of dimethyl-formamide (DMF). To this solution were added 5 ml water and if a precipitate appeared the DMF concentration was increased until a clear solution was obtained. The solution was acidified by the addition of 1 ml concentrated sulfuric acid followed by 200 ml amyl nitrite. After 30 minutes of stirring at 4° C., sodium azide (200 mg in 4 ml water) was added. The mixture was stirred and cooled for a further 30 minutes and then a saturated solution of sodium chloride was added until a volume of 20 ml was reached. The dark red precipitate was filtered and washed with a cold solution of sodium chloride. All steps of this preparation were performed under a red light. Yield: 70 mg.

Azidofluorescein Diacetate

Azidofluorescein (50 mg) was dissolved in 2 ml dry pyridine and to this solution was added 1 ml freshly distilled acetic anhydride. The mixture was allowed to stand overnight at room temperature and then poured into crushed ice. The orange-red precipitate was filtered, washed with cold water and dried in vacuo. All steps of this preparation were carried out under a red light. Yield: 40 mg.

Azidofluorescein easily penetrates into living cells, and when irradiated after such penetration at a wavelength greater than 3000 nm, the azidofluorescein is converted to the active nitrene species which is coupled to proteins.

I claim:
1. Azidofluorescein diacetate.
2. Azidofluorescein.

* * * * *